US010435486B2

(12) United States Patent
Sellergren et al.

(10) Patent No.: US 10,435,486 B2
(45) Date of Patent: Oct. 8, 2019

(54) POLYMERS PREPARED USING SMART TEMPLATES

(71) Applicant: Boerje Sellergren, Helsingborg (DE)

(72) Inventors: Borje Sellergren, Helsingborg (SE); Melanie Berghaus, Dortmund (DE)

(73) Assignee: Boerje Sellergren, Helsingborg (SE)

( * ) Notice: Subject to any disclaimer, the term of this patent is extended or adjusted under 35 U.S.C. 154(b) by 0 days.

(21) Appl. No.: 15/428,091

(22) Filed: Feb. 8, 2017

(65) Prior Publication Data

US 2017/0145133 A1 May 25, 2017

Related U.S. Application Data

(62) Division of application No. 14/748,358, filed on Jun. 24, 2015, now abandoned.

(30) Foreign Application Priority Data

Jun. 26, 2014 (SE) ........................ 1430090

(51) Int. Cl.
*C08F 2/44* (2006.01)
*G01N 33/545* (2006.01)
*C08F 220/54* (2006.01)
*C08F 292/00* (2006.01)
*C08F 220/56* (2006.01)
*C08F 222/14* (2006.01)

(52) U.S. Cl.
CPC .............. *C08F 2/44* (2013.01); *C08F 220/54* (2013.01); *C08F 220/56* (2013.01); *C08F 222/14* (2013.01); *C08F 292/00* (2013.01); *G01N 33/545* (2013.01); *G01N 2600/00* (2013.01)

(58) Field of Classification Search
CPC ...... C08F 2/44; C08F 292/00; G01N 2600/00
See application file for complete search history.

(56) References Cited

U.S. PATENT DOCUMENTS

2002/0198349 A1* 12/2002 Norton .................. B01D 15/00
526/319
2004/0157209 A1* 8/2004 Yilmaz .................. B01J 20/26
435/5
2012/0270964 A1 10/2012 Piletsky et al.

FOREIGN PATENT DOCUMENTS

CN 103524742 A * 1/2014

OTHER PUBLICATIONS

Harris, Constance et al "Vancomycin: Structure and Transformation to CDP-I" Journal of the American Chemical Society, 1983 vol. 105 No. 23 p. 6915-6922) (Year: 1983).*
Berghaus, M., et al., "Productive encounter: Molecularly imprinted nanoparticles prepared using magnetic templates", "Chemical Communications", Jun. 25, 2014, pp. 8993-8996 (Author Manuscript), vol. 50.
Hoshino, Y., et al., "Affinity Purification of Multi Functional Polymer Nanoparticles", "J Am Chem Soc", Oct. 6, 2010, pp. 13648-13650 (Author Manuscript), vol. 132, No. 39.

(Continued)

*Primary Examiner* — Ling Siu Choi
*Assistant Examiner* — David L Miller
(74) *Attorney, Agent, or Firm* — Hultquist, PLLC; Steven J. Hultquist

(57) ABSTRACT

New molecularly imprinted polymers are described, and a method for their production using novel particle technology based on multifunctional placeholder templates.

13 Claims, 10 Drawing Sheets

(56) References Cited

OTHER PUBLICATIONS

Note: For the non-patent literature citations that no month of publication is indicated, the year of publication is more than 1 year prior to the effective filing date of the present application.
Poma, A., et al., "Solid-Phase Synthesis of Molecularly Imprinted Polymer Nanoparticles with a Reusable Template—'Plastic Antibodies'", "Adv. Funct. Mater.", Jan. 16, 2013, pp. 2821-2827, vol. 23.
Wulff, G., et al., "Soluble Single-Molecule Nanogels of Controlled Structure as a Matrix for Efficient Artificial Enzymes", "Angew. Chem. Int. Ed.", 2006, pp. 2955-2958, vol. 45.
Unpublished U.S. Appl. No. 14/748,358, filed Jun. 24, 2015.
Note: As to any co-pending U.S. applications cited herein, Applicant will provide at the examiner's request copies of any documents desired by the examiner from the USPTO file history of any such co-pending applications.

* cited by examiner

POLYMERS PREPARED USING SMART TEMPLATES

CROSS-REFERENCE TO RELATED APPLICATIONS

This is a divisional application under 35 U.S.C. § 120 of U.S. patent application Ser. No. 14/748,358 filed on Jun. 24, 2015, which in turn claims priority under the provisions of 35 U.S.C § 119 to Swedish Patent Application No. 1430090-9 filed on Jun. 26, 2014. The disclosures of U.S. patent application Ser. No. 14/748,358 and Swedish Patent Application No. 1430090-9 are hereby incorporated herein by reference, in their respective entireties, for all purposes.

TECHNICAL FIELD

The present describes new molecularly imprinted polymers and a method for their production using novel particle technology based on multifunctional placeholder templates.

BACKGROUND ART

Molecular imprinting refers to a templating technique for producing inverse replicas of individual molecules in network polymer. This approach has been used to generate porous materials exhibiting receptor-like affinity for a large variety of template structures. Commonly referred to as plastic antibodies, these can now be produced of a similar size and featuring binding properties resembling antibodies. Their ability to function in complex environments including biological environments in vivo has therefore considerably expanded their scope of applications, mainly as antibody substitutes in assays, sensors, separations and as a new class of drugs or therapeutic tools. The development of new and improved methods for producing these receptors is hence an urgent goal, from both an industrial and societal perspective.

Most examples of high fidelity molecular imprinting have been demonstrated using highly cross-linked organic polymers as the imprinting matrix. Free radical polymerization of functional vinyl monomers with an excess of cross-linking divinyl monomers in presence of a porogen, usually a solvent for the monomers, has for long been the method of choice to produce these materials. To form the binding sites, a template or template-monomer adduct is added prior to polymerization. Subsequent removal of the template results in a porous organic polymer material equipped with binding sites for the template ion or molecule.

One recurring problem associated with molecularly imprinted polymers (MIPs) is viewed when testing the reuptake of template to the empty binding sites. Here, a strong dependence of the partition coefficient on the sample load is commonly seen. The origin behind this effect is in most cases a heterogeneous distribution of binding sites. In non-covalent imprinting, two effects contribute primarily to the binding site heterogeneity. Due to the amorphous nature of the polymer, the binding sites are not identical, somewhat similar to a polyclonal preparation of antibodies. The sites may, for instance, reside in domains with different cross-linking density and accessibility. Secondly, this effect is reinforced by the incompleteness of the monomer-template association.[5] In most cases the major part of the functional monomer exists in a free or dimerized form, not associated with the template. As a consequence, only a part of the template added to the monomer mixture gives rise to selective binding sites. The low yield of binding sites results in a strong dependence of selectivity and binding uptake on sample load.

Template occlusion is another recurring problem in traditional molecular imprinting. Typically a small fraction of the template added to the monomer mixture remains entrapped or bound in the polymer matrix which can result in bleeding—a process detrimental when using the MIPs as enrichment phases in trace analysis. Moreover, template recovery is not straightforward requiring multiple purification steps. This is unpractical and costly in cases where expensive templates are used.

Finally, even when approaches are found successfully addressing each of the aforementioned problems, the final imprinting technique should be economically attractive, and scalable i.e. allowing facile scale up to meet industrial demands. Since developing a new MIP is an interative process, several MIPs needs to be synthesized and screened before the right one is found. This optimization requires parallel synthesis protocols and miniaturization which are other criteria for a practical imprinting technique.

Several approaches have been assessed in order to overcome the aforementioned problems. Hardly avoidable, the kinetically controlled formation of the polymer network leads to a statistical distribution of binding site microenvironments. One way to overcome this problem is to use polymer matrices formed by thermodynamically controlled reversible polymerization reactions. Controlled radical polymerization (CRP) may offer benefits in this regard.[8] CRP distinguish itself relative conventional radical polymerization in the low active radical concentration and the life time of the growing radical. This allows the preparation of polymers with predefined molecular weights, low polydispersity, controlled composition and functionality. Other ways to reduce the polyclonality of imprinted sites have been suggested. A particularly simple approach in this context is to thermally cure or anneal the polymers which was anticipated to cause polymer chain relaxation leading to enhanced thermodynamic control of the binding site formation. Another approach was the use of high pressure polymerizations anticipating that this would stabilize the monomer template complexes and thus reduce heterogeneity caused by this factor.

Alternatively, the template may be confined by immobilization at a solid liquid interface or liquid liquid interface.[12] This technique is referred to as interfacial imprinting and presumably leads to a more defined microenvironment due to the restricted template mobility during polymerization and subsequent removal of the poreforming phase.

Finally, nanoparticles or nanogels produced by precipitation, emulsion or graft polymerization, and thin film materials may exhibit more homogenous binding sites due to the spatial restrictions imposed by the limited film thickness or microgel radius. Furthermore by reducing the size of the MIP to form particles in the nanometer range, for very small particles referable to as soluble MIPs, MIPs with on average one site per particle can be produced. In such systems heterogeneity is mainly due to the non-equivalence of sites between the particles (cf. polyclonal antibodies) and as polyclonal antibodies the particles can be fractionated and enriched by affinity chromatography. Miniemulsion polymerization protocols can be used for interfacial imprinting of such nanoparticles, hence combining the advantages of the nanoparticle format, and interfacial imprinting.

In spite of the above individually promising results, none of the reported methods address the remaining problems i.e. 1) template occlusion and recycling and 2) process scalability and 3) parallelism and miniaturization. There is therefore a need for new techniques allowing simultaneously interfacial imprinting, nanoparticle production, template recycling and parallelism and scalability.

SUMMARY

The objective of the present disclosure is to be able to prepare molecularly imprinted polymers (MIPs) in high yield, for any given template, in the form of nano- or micro-particles where the MIPs should exhibit a unique affinity for a given target and should be obtained in a template free form. The objective is also to be able to prepare the MIPs using a scalable process allowing practical and economic recycling and reuse of the template. Moreover the process can be miniaturized allowing several MIPs to be prepared in parallel. The objective is achieved by the here disclosed method relying on the use of nanosized multifunctional and recyclable placeholder templates (FIG. 1). The use of such templates allows a facile enrichment of imprinted particles according to their affinity in a template free form. Compared to alternative techniques relying on solid phase synthesis of MIP nanoparticles, the current protocol, inherited in the enhanced effective concentration of the placeholder templates, allows multiple parallel reactions to be performed using a scalable process.

This disclosure thus describes a new generic and scalable method to prepare surface imprinted polymer micro and nanoparticles which potentially overcomes previous imprinting technology hurdles e.g. template removal and recycling, heterogenous binding sites, low binding affinity and poor site accessibility.

DEFINITIONS

Figure 1:
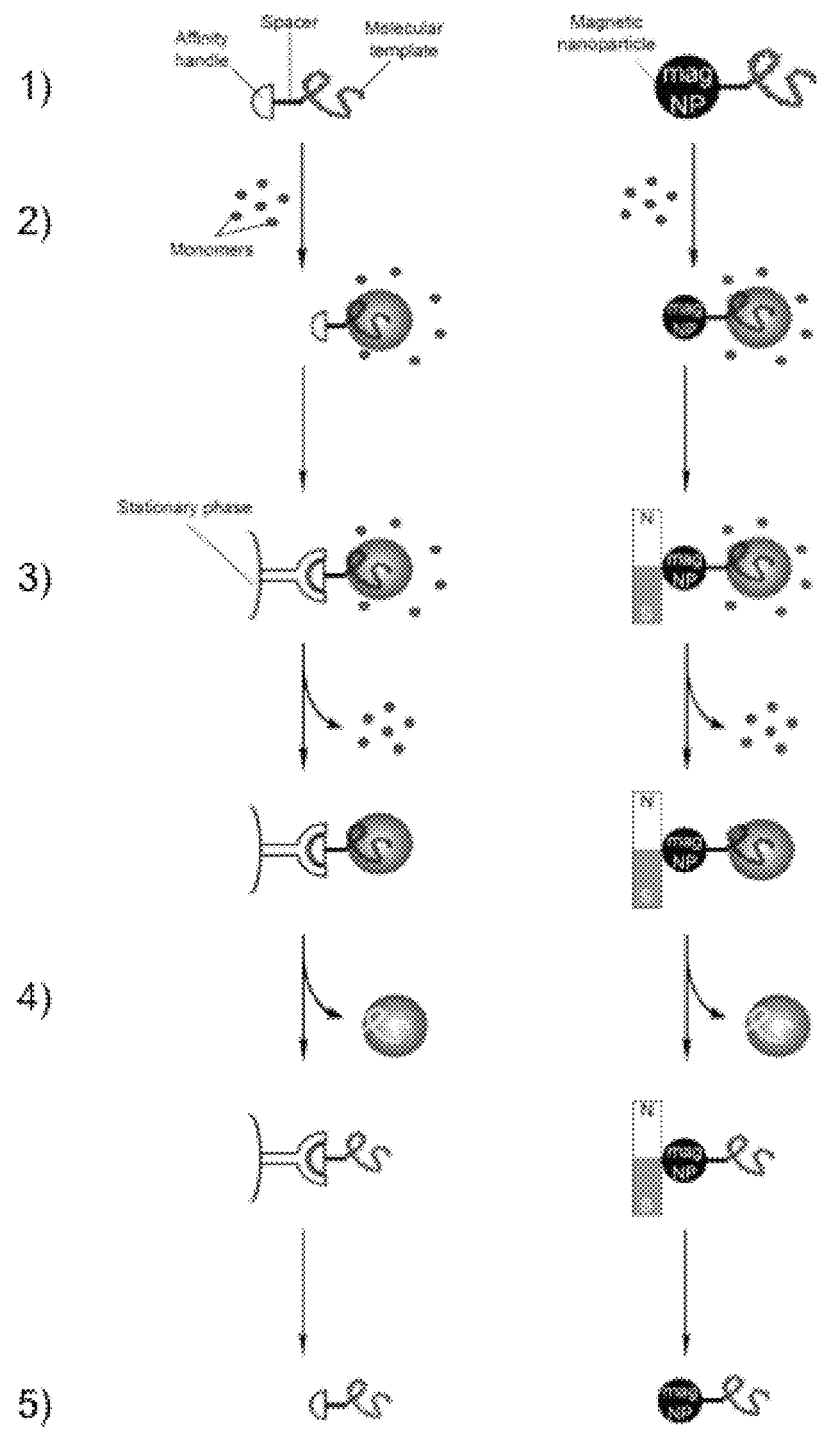
FIG. 1 is a schematic representation of the sequence of steps in an illustrative process of using multi-functional placeholder templates for affinity enrichment using either chemical (left) or magnetic (right) affinity handles and purification of the resulting surface imprinted micro and nanoparticles. The steps in the process include: (1) providing a multifunctional placeholder template; (2) polymerizing at least one monomer, optionally dissolved in a solvent, in presence of the multifunctional placeholder template; (3) separating the multifunctional placeholder template and polymers adhering to the multifunctional placeholder template from the crude reaction mixture; (4) gradually releasing the polymer adhering to the multifunctional placeholder template by physical or chemical techniques, thereby allowing to enrich polymers (MIPs) which bind strongly to the multifunctional template; and (5) reuse of the multifunctional placeholder template repeating steps 1-4.

A "polymerizable group" is a group of atoms forming part of a monomer capable of reacting with itself or with other monomers to form a polymer.

"Specific binding" of a MIP mean that the MIP exhibits appreciable affinity for a target or a small group of targets or a preferred epitope and, preferably, does not exhibit significant cross-reactivity.

A MIP that "does not exhibit significant cross reactivity" is one that will not appreciably bind to an undesirable entity (e.g., an undesirable proteinaceous entity). Specific binding can be determined according to any art-recognized means for determining such binding.

The term "epitope" refers to a site on a target peptide or protein to which, in analogy with antibodies, the MIP specifically binds. An epitope typically includes at least 3, 4, 5, 6, 7, 8, 9, 10, 11, 12, 13, 14 or 15 amino acids.

A "support", in the context of producing a MIP formats, refers to any inorganic support e.g. silica, alumina, porous glass, titania or an organic polymer support of any form, e.g., particles, nanoparticles, nanofibers, planar supports, nanotubes.

"Nanoparticles" refers to inorganic or organic particles with an average size smaller than 1 µm (particle diameter).

An "affinity handle" is a group on a molecule in a crude mixture that binds specifically to a ligand immobilized on a stationary phase or to a magnetic surface.

An "Antigen" (Immunobiology) is a substance that evokes the production of antibodies.

An "Assay" is a standardized reaction procedure for the qualitative and quantitative detection of an analyte (pharmaceutics, molecular biology)

"Controlled radical polymerization (CRP)" is a polymerization method in which the determination reaction is reversible, thus allowing to achieve a predetermined molecular weight and narrow molecular weight distributions over a wide range of monomers.

An "ELISA" is an enzyme linked immunosorbent assay.

An "Inhibitor" is a substance that decreases the rate of, or prevents, a chemical reaction.

"Interfacial imprinting" is molecular imprinting with the template immobilized on a solid or in a liquid phase and the polymerization taking place in a second phase.

A "Ligand" forms a complex with a biomolecule, usually to serve a biological purpose.

"Miniemulsion polymerization" is a method for the production of polymer nanoparticles via a liquid-liquid two phase system.

"Molecularly imprinted polymers (MIPs)" Polymer that has been processed using the molecular imprinting technique which leaves cavities in polymer matrix with affinity to a chosen "template" molecule.

"Nanogels/microgel" Nanoparticles or microparticles, respectively, composed of a hydrophilic polymer network.

The "Partition coefficient" is Ratio of concentrations of a compound in a mixture of two immiscible phases at equilibrium, e.g. template bound to MIP and free template in solution.

"Placeholder templates" are molecular template connected via a spacer to an affinity handle.

"Spacer" is an inert group of atoms separating the affinity handle from the molecular template e.g. an alkyl chain, an oligoethylenglycol chain, a polyethylenglycol chain, a polyglycerol chain.

"Plastic antibodies" are polymer particles in the size of antibodies that have a high binding affinity to an antigen.

"Polyclonal antibodies" are antibodies which bind to different regions of the same target molecule.

"Polydispersity" refers to an inconsistent shape, size and molecular weight distribution of objects, here particles.

A "(Protein immobilized) Sacrifical porous support ((P) SPS)" in the context of producing a MIP formats, refers to any inorganic scaffold, e.g., silica, alumina, porous glass, titania or an organic polymer support of any form, e.g., particles, nanoparticles, nanofibers, planar supports, nanotubes.

A "Spacer" connects two moieties of a molecule.

A "Stationary phase" is a substance fixed in place in a chromatography procedure.

A "Target" in the context of MIPs is the molecule which should be bound by a MIP. This is not necessarily identical with the template (epitope approach).

DETAILED DESCRIPTION

According to the present disclosure, there is provided a surface imprinted polymer characterized in that it is obtainable by:
1) providing a multifunctional placeholder template;
2) polymerizing at least one monomer, optionally dissolved in a solvent, in presence of the multifunctional placeholder template;
3) separating the multifunctional placeholder template and polymers adhering to the multifunctional placeholder template from the crude reaction mixture;
4) gradually releasing the polymer adhearing to the multifunctional placeholder template by physical or chemical means thereby allowing to enrich polymers (MIPs) which bind strongly to the multifunctional template; and
5) reuse of the multifunctional placeholder template repeating steps 1-4.

Figure 2:
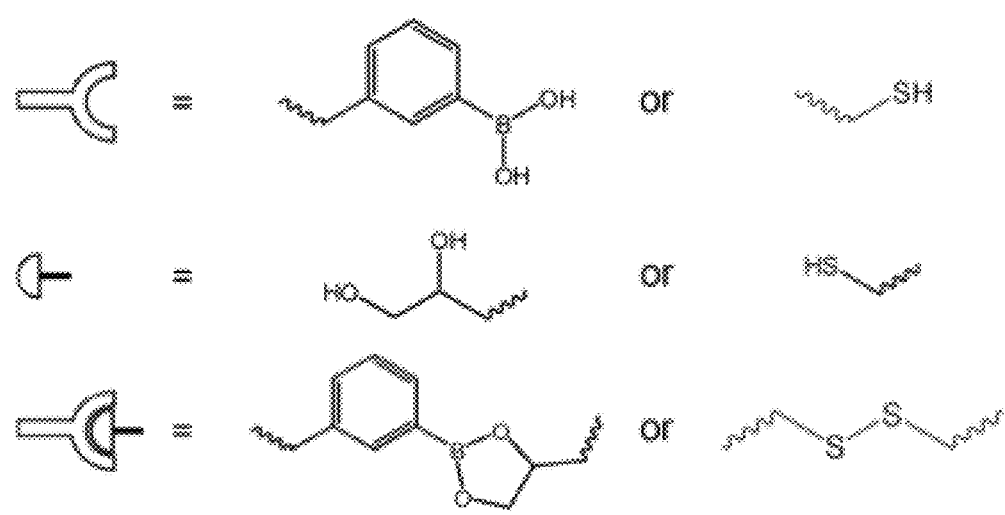
FIG. 2 is a depiction of chemical affinity handles for use in multifunctional placeholder templates based reversible boronate ester (left) or disulfide (right) formation.

In one embodiment, the disclosure refers to a surface imprinted polymer wherein the multifunctional placeholder template is composed of a molecular template connected via a spacer to an affinity handle (FIGS. 1 and 2).

In one embodiment, the disclosure refers to a surface imprinted polymer wherein the molecular template is characterized in that it consists of a molecular structure representing the target molecule or a fragment of the target molecule such as an epitope.

In one embodiment, the disclosure refers to a surface imprinted polymer wherein the molecular template is a peptide possibly representing an epitope of a target protein.

In one embodiment, the disclosure refers to a surface imprinted polymer wherein the molecular template is a glycan possibly representing a glycosidic fragment of an oligosaccharide or a glycoprotein.

In one embodiment, the disclosure refers to a surface imprinted polymer wherein the molecular template is an oligonucleotide or a mimic of an oligonucleotide.

In one embodiment, the disclosure refers to a surface imprinted polymer wherein the spacer is characterized in that it is sufficiently long for the multifunctional placeholder template to bind the adheared polymer and to the stationary phase.

In one embodiment, the disclosure refers to a surface imprinted polymer wherein the spacer is characterized in that it can consist of polyethylenglycol, polyglycerol, poly-2-hydroxymethacrylate or a perfluorinated hydrocarbon chain.

In one embodiment, the disclosure refers to a surface imprinted polymer wherein the spacer can be prepared by controlled radical polymerization (e.g. iniferter, RAFT, ATRP, NMP) allowing the molecular template or the affinity handle to be attached by endgroup functionalization In one embodiment, the disclosure refers to a surface imprinted polymer wherein the affinity handle is characterized in that it can bind reversibly to functional groups of a solid stationary phase or of one of the phases of a liquid liquid two phase system.

In one embodiment, the disclosure refers to a surface imprinted polymer wherein the affinity handle consists of one or several vicinal diol groups or another functional group capable of reversibly forming ester bonds with a boronic acid ligand (FIG. 2).

In one embodiment, the disclosure refers to a surface imprinted polymer wherein the affinity handle consists of a thiol or protected thiol group capable of reversibly binding to a disulfide containing stationary phase for instance 2-pyridyldisulfide functionalized stationary phase (FIG. 2).

In one embodiment, the disclosure refers to a surface imprinted polymer wherein the affinity handle is magnetic.

In one embodiment, the disclosure refers to a surface imprinted polymer wherein the affinity handle is a magnetic particle (FIG. 1).

In one embodiment, the disclosure refers to a surface imprinted polymer prepared by any of the procedures referred to as precipitation polymerization, miniemulsion polymerization or grafting from polymerization.

In one embodiment, the disclosure refers to a surface imprinted polymer prepared by the technique of reversible addition fragmentation chain transfer polymerization (RAFT).

In one embodiment, the disclosure refers to a surface imprinted polymer wherein the separation of the multifunctional placeholder template and polymers adhering to the multifunctional placeholder template from the crude reaction mixture is performed by allowing the crude reaction mixture containing the multifunctional placeholder template to contact a solid stationary phase which is capable of reversibly binding to the affinity handle of the multifunctional placeholder template, thereby leading to separation of the multifunctional placeholder template and particles adhering to the multifunctional placeholder template from the crude reaction mixture (FIG. 1).

In one embodiment, the disclosure refers to a surface imprinted polymer wherein the separation of the multifunctional placeholder template and polymers adhering to the multifunctional placeholder template from the crude reaction mixture is performed by allowing the crude reaction mixture containing the multifunctional placeholder template to be exposed to a magnetic field resulting in magnetic separation of the multifunctional placeholder template and particles adhering to the multifunctional placeholder template from the crude reaction mixture.

In one embodiment, the disclosure refers to a surface imprinted polymer wherein gradually releasing the polymer adhering to the multifunctional placeholder template is achieved by increasing or reducing temperature.

In one embodiment, the disclosure refers to a surface imprinted polymer wherein gradually releasing the polymer adhering to the multifunctional placeholder template is achieved by subjecting the separated placeholder template to solutions of increasing ionic strength, organic solvents or organic solvents with modifiers of increasing concentration.

In one embodiment, the disclosure refers to a surface imprinted polymer wherein gradually releasing the polymer adhering to the multifunctional placeholder template is achieved by subjecting the separated placeholder template to solutions containing an increasing concentration of a displacer molecule.

In one embodiment, the disclosure refers to a surface imprinted polymer containing thiol groups which can be quantified by established thiol assays.

The present disclosure also provides a process for the preparation of a molecularly imprinted polymer, characterized by
1) providing a multifunctional placeholder template;
2) polymerizing at least one monomer, optionally dissolved in a solvent, in presence of the multifunctional placeholder template.
3) Separating the multifunctional placeholder template and polymers adhering to the multifunctional placeholder template from the crude reaction mixture
4) Gradually releasing the polymer adhering to the multifunctional placeholder template by physical or chemical means
5) Reuse of the multifunctional placeholder template repeating steps 1-4.

The present disclosure also provides a use of the surface imprinted polymers and/or multifunctional placeholder templates:
in separations
in sensors for molecular targets in terms of identity and concentration.
In assays (e.g. ELISA)
as in vivo or in vitro imaging or contrast agent
as detection tool in electrophoresis
as therapeutic agents (e.g. as drugs)
as catalysts In one embodiment the surface imprinted polymers and multifunction placeholder templates are used in competitive assays or sensors relying on electrochemical or magnetic detection principles

EXAMPLES

Example 1

Preparation of a Magnetic Core Silica Shell Nanoparticles (magNP@SiO2)

Synthesis of magnetic core particles: 6 g $FeSO_4.7H_2O$ and 7 g anhydrous $FeCl_3$. were dissolved in 200 ml millipore water under $N_2$ with vigorous stirring at 85° C. 15 mL of 25% ammonia (aq) were added quickly into the solution. The solution turned from orange to black due to the precipitation of the magnetite nano-particles. The solution was stirred for 30 min at elevated temperature and then allowed to cool down to RT. Afterwards, the magnetic particles were collected using a magnet and washed with 3×50 mL water and finally with 50 mL 0.2M NaCl solution. The particles were dried at 80° C. under vacuum.

Synthesis of magnetic core silica shell particles (magNP@SiO2): 2 g of dry magNP were dispersed in 50 mL water by sonication. Then they were collected by a magnet and the supernatant was removed. Then, a 10% (v/v) TEOS-solution (230 mL) was added followed by 200 mL glycerol. The pH was adjusted to 4.6 with glacial acetic acid. Afterwards, the mixture was heated to 90° C. under $N_2$ atmosphere and stirred using an over head stirrer for 2 hours. The particles were collected while the mixture was still hot, because the increasing viscosity of the suspension due to the glycerol by cooling to room temperature makes the removal of the particles difficult due to increased viscosity. After washing with water (3×200 mL) and ethanol (3×100 mL), the particles were dried in a vacuum oven at 40° C. The presence of silica on the particles has been confirmed by FT-IR.

Example 2

Functionalization of the Magnetic Silica Core-Shell Beads with Glycidoxypropyltrimethoxysilane (GPTMS) to Give magNPepoxy 3.25 g magNP@SiO2 were dispersed in 50 mL dry toluene under $N_2$-atmosphere by sonication. 1 mL GPTMS was added to the solution and the mixture was heated to reflux under positive nitrogen pressure and stirred using an overhead-stirrer for 30 h. Then, the particles were collected using a magnetic separator and washed with 3 times with 50 mL toluene and 3 time with 50 mL acetone and dried under vacuum at 40° C.

Example 3

Figure 3:
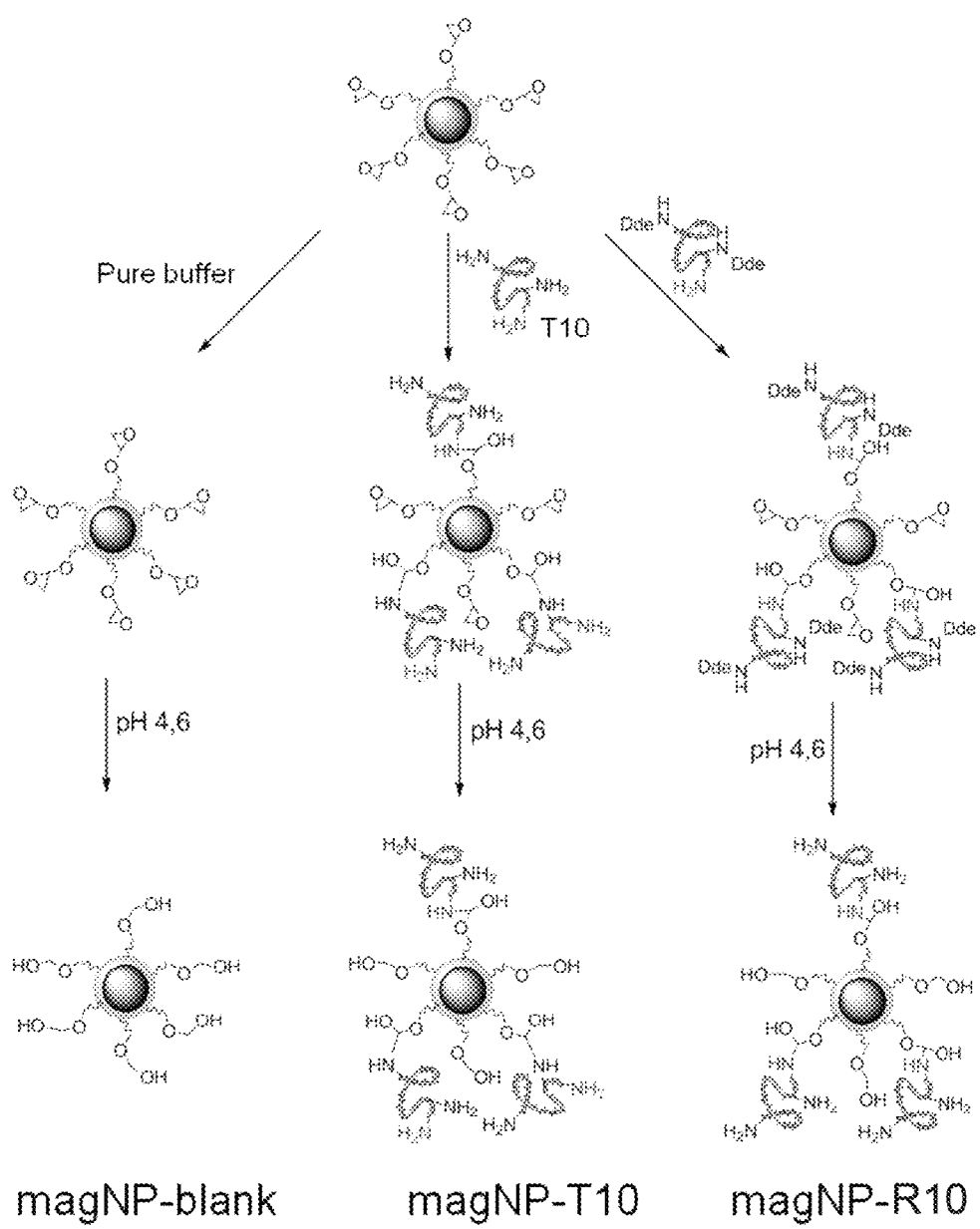
FIG. 3 is a representation of a synthesis route of the three magnetic nanoparticles magNP-blank, magNP-T10 and magNP-R10 starting from the epoxy-modified magnetic silica shell particles. The N-Terminus is colored in red, the primary amines of the side chains in black. The residual epoxy-rings were opened through incubation in acetic buffer.

Immobilization of the Decapeptides $NH_2$-Q-K—S-L-S-L-S—P-G-K—COOH (T10) and $NH_2$-Q-L-S—K—S—K—S—P-G-L-COOH (R10) on the Magnetic Nanoparticles to Give magNP-T10 and magNP-R10 (FIG. 3).

Figure 4:
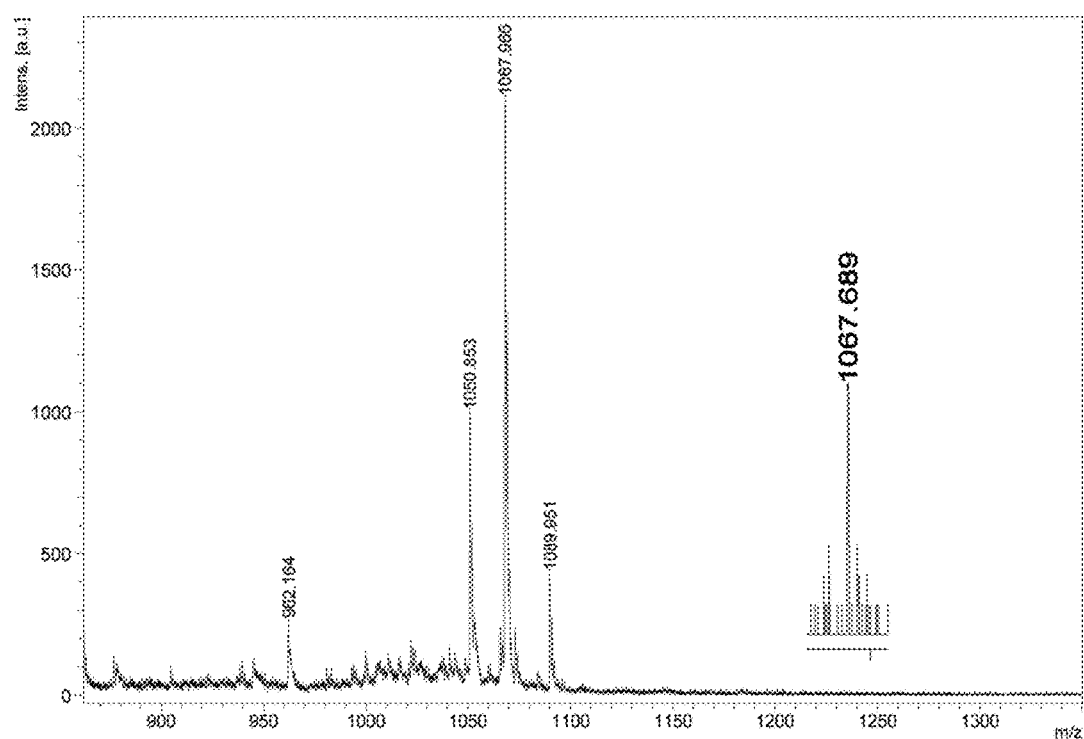
FIG. 4 is a spectrum of MALDI TOF-Spectra of T10 on magnetic particle (large spectrum) pure T10 (insert).

1 g of epoxy-functionalized magnetic particles were dispersed In buffer (phosphate buffer, pH 7.4) (5 mL) by sonication. They were separated using a magnet and the supernatant was discarded. Then, a solution of 5.3 mg T10 or R10 in 5 mL of the same buffer was added to the magnetic particles. Also a blank sample was prepared by adding 5 mL pure buffer. The three samples were incubated over night at RT on a shaker. MALDI TOF analysis of the nanoparticle samples with reference to free peptide demonstrated the successful immobilization (FIG. 4).

Example 4

Immobilization of L- or D-Phenylalanine Anilide (PA) on the Magnetic Nanoparticles (magNP-LPA and magNP-DPA)

150 mg of epoxy-modified magNP (see Example 2) was incubated in 1 mL of a 1 mg/mL solution of LPA or DPA, respectively, in toluene over night at 50° C. Afterwards, the magNP were washed with toluene and MeOH and dried.

Example 5

Figure 5:
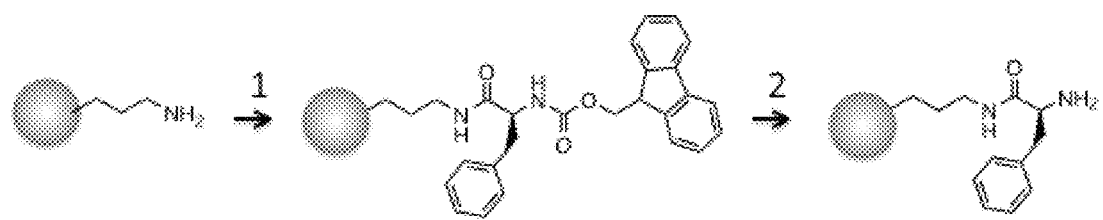
FIG. 5 is a graphic depiction of the immobilization of L-Phenylalanine on amino-functionalized magnetic nanoparticles (magNP-LPAc); 1) Fmoc-L-Phe, DCCI, DMF; (2) piperidine in DMF.

Immobilization of L-Phenylalanine on Aminofunctionalized Magnetic Nanoparticles (magNP-LPAc) (FIG. 5)

Aminofunctionlization: 1 g magNPs@SiO2 were sonicated in 30 mL ethanol/water (volume ratio, 1:1) solution for 30 min to get uniform dispersion. Then 4 mL aminopropyltrimethoxysilane (APTMS) was added to the solution under N2 atmosphere at 40 C over night (Incubator). The optimal surface modification molar ratio of APTMS to Fe3O4 was found 4:1. After that the solution was cooled to room temperature. The prepared APTMS-modified magNPs were collected with a magnet, and washed with ethanol, followed by deionized water for three times. Finally, APTMS-modified Fe3O4NPs were dried under vacuum at 60° C.

Coupling of Phenylalanine: 1.9 mg Fmoc-Phe-OH was incubated with 10 mL of a 5 mM EDC and 10 mM N-hydroxysuccinimide (NHS)-solution in 50 mM Phosphate buffer, pH 7.5 for 15 min to form the active ester. This solution was added to 500 mg magNP-NH2. After 10 min of sonication, the particles were incubated over night at room temperature. The Fmoc group was cleaved off by treating the particles in 5 mL of a 20% piperidine solution in DMF.

Example 6

Synthesis of RAFT Modified Core Particles (SiNP-RAFT)

A suspension (25 mL, 7.5 g) of 30 wt % colloidal silica nanoparticles was added to a three-necked round-bottom flask with 3-aminopropyldimethylethoxysilane (0.62 g, 3.7 mmol) and 40 mL of dried THF. The reaction mixture was heated at 85° C. under $N_2$ protection overnight and then cooled to room temperature. The reaction mixture was precipitated into a large amount of hexanes (500 mL). The particles were recovered by centrifugation at 3000 rpm for 15 min. The particles were then redissolved in 40 mL of acetone and reprecipitated in 300 mL of hexanes. The aminofunctionalized particles were dispersed directly into 70 mL of THF for subsequent use. 0.168 g of CPDB (4-cyano-4-(thiobenzoylthio)pentanoic acid) (0.604 mmol), 57.82 µL of ethylchloroformate (0.604 mmol) and 84.29 µL of triethylamine (TEA) (0.604 mmol) were added in a three necked flask with 50 mL of THF. The system was purge with $N_2$ and cooled in an ethanol-liquid nitrogen bath for 40 minutes at −70° C. After that, 7.176 g (65 mL) of amino modified silica (0.604 mmol of amino groups) were added at −10° C. and the reaction was leaved overnight. After that, the particles were precipitated in hexane (500 mL) and collected by centrifugation (3500 rpm, 15 min). Then, they were re-suspended in acetone (80 mL), precipitated again in 300 mL of hexane, centrifugated at 3500 rpm during 15 min, and re-suspended in 100 mL THF.

An aliquot of the RAFT-functionalised colloidal silica nanoparticles was dried and subjected to thermal gravimetric analysis to determine the amount of RAFT agent anchored onto the particles (0.086 mmol/g).

Example 7

Synthesis of Core Shell MIPs Using an L-PA Placeholder Template or Soluble L-PA

SiNP-RAFT particles (100 mg) were suspended in a prepolymerization mixture containing either L-PA (3 mg) (NP-MIP1), or magNP-LPAc (50 mg) (NP-MIP2), MAA (8.6 µL) and EDMA (95 µL) dissolved in 3 mL of dry toluene. Nonimprinted particles were produced identically but leaving out L-PA for NP-MIP1 (NP-N1) or by using ring opened magNPepoxy (NP-N2). The polymerization mixture was subjected to three freeze-thaw cycles under nitrogen where after the initiator ABDV (0.9 mg), was added. This corresponds to a ratio of RAFT/initiator of 3. Polymerization was initiated at 50° C. and allowed to proceed for 22 h. Template removal and isolation of the NP-MIPs were then performed as follows:

NP-MIP1 (NP-N1): After polymerization, template removal was carried out by 4 steps washing with 15 mL (MeOH 80%, Formic Acid 15%, 5% H2O) each time incubate 1 h and centrifuging at 5000 rpm. The final step washing was carried out with pure methanol (15 ml) for 30 min. All the supernatants were collected and checked by HPLC to monitor template removal. Thereafter the particles were subjected to aminolysis by butylamine followed by washing with acetonitrile, centrifugation and finally drying under vacuum at 40° C.

Figure 6:
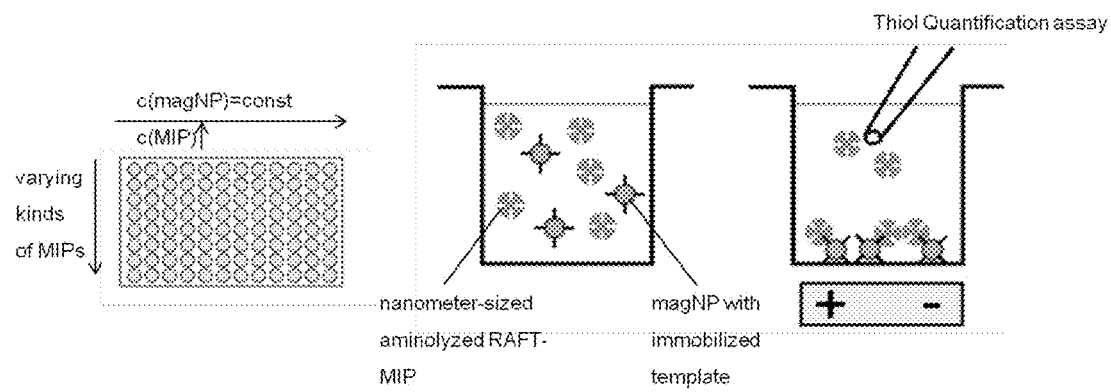
FIG. 6 schematically depicts a thiol-based binding assay (Ellman assay) between magnetic nanoparticles and aminolyzed RAFT-MIPs.
Figure 7:
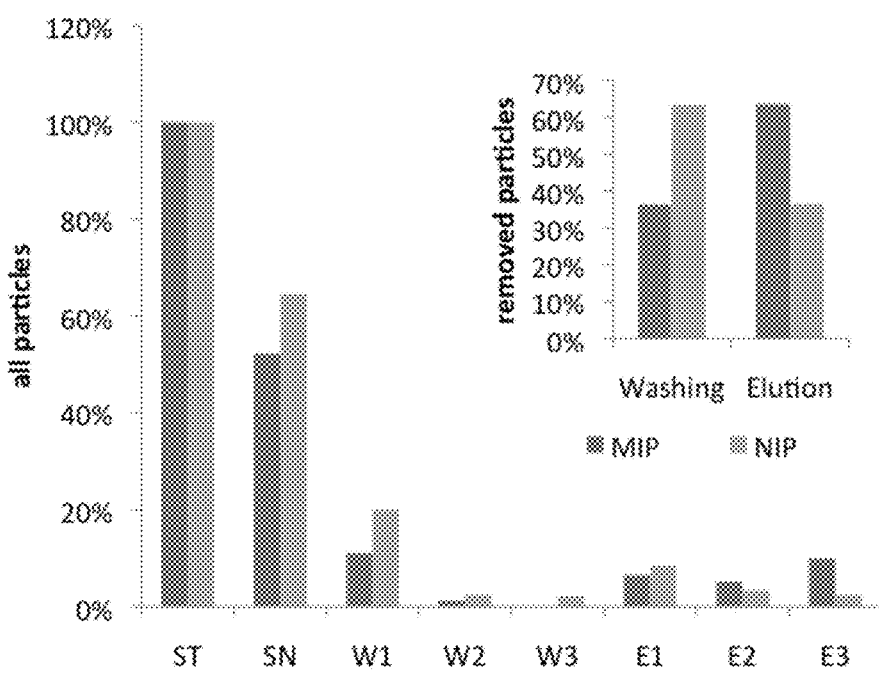
FIG. 7 is a graph of the distribution of nanoparticles NP-MIP2 (red bars) and NP-N2 (green bars) in the fractions resulting from gradual washing and elution of particles attached to magNP-LPAc (NP-MIP2) and ring-opened magNPepoxy (NP-N2). ST=total amount of NPs, SN=amount of NPs remaining in supernatant after polymerization and separation of magnetic fraction, W1-3=washing with 500 µL acetonitrile, E1-E3=elution with MeOH/water/formic acid: 80/15/5 (E1); 80/10/10 (E2) and 80/5/15 (E3). The particle concentration was determined by the Ellman thiol assay.
Figure 8:
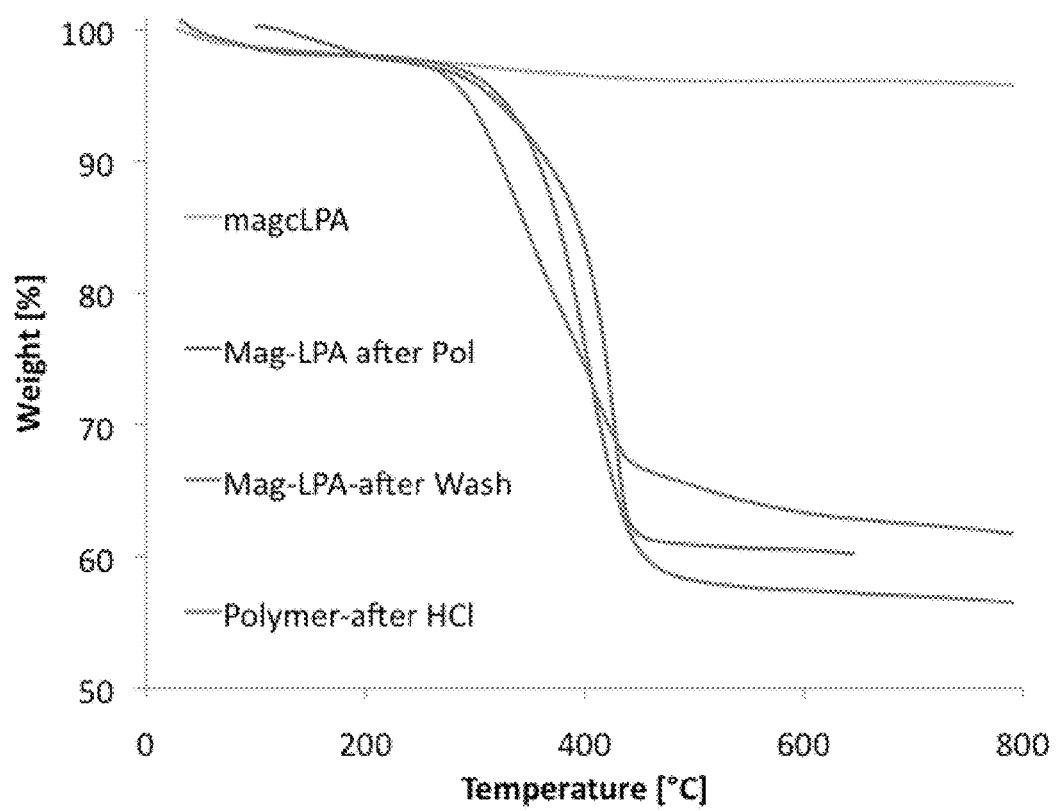
FIG. 8 is a graph of the thermal gravimetric analysis of nanoparticles and nanoparticle aggregates in Example 7.

NP-MIP2 (NP-N2): After polymerization the particles were collected by magnet, subjected to aminolysis with butylamin and thereafter resuspended in Acetonitrile (500 µL, at room temperature). The supernatant was removed after magnetic separation of the particles, fresh 500 µL MeCN was added and the solution was heated for 10 min at 30° C. under sonication. The particles were then again collected, fresh solvent was added and the same procedure was repeated in steps of 10° C. until 60° C. were reached. After this, the magNP were washed with a MeOH solutions containing 5%, 10% and 15% formic acid (FA) respectively, again for 10 min under sonication at room temperature. All solutions were included in a thiol assay (Ellman assay) to quantify the amount of eluted particles in each solution (FIG. 6). It could be shown that the FA seems to favor the elution of the particles (FIG. 7) and that NP-N2 had a lower affinity for the magNPs. Thermal gravimetric analysis of the different particle aggregates prove that polymer is removed in the elution step (FIG. 8).

Example 8

Test of NPs According to Example 7 for Their Affinity for L-PA and D-PA.

Figure 11:
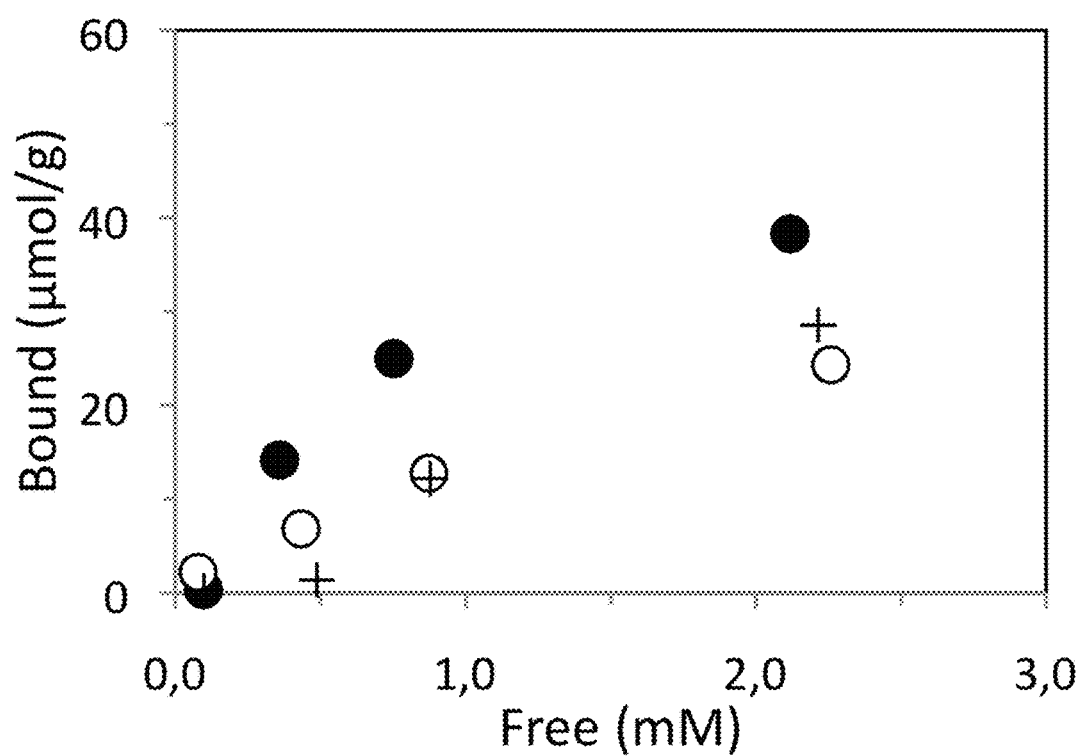
FIG. 11 is a graph of binding curves of L-PA (solid symbols) and D-PA (open symbols) on L-PA imprinted SiNP-MIP1 and SiNP-NIP1.
Figure 12:
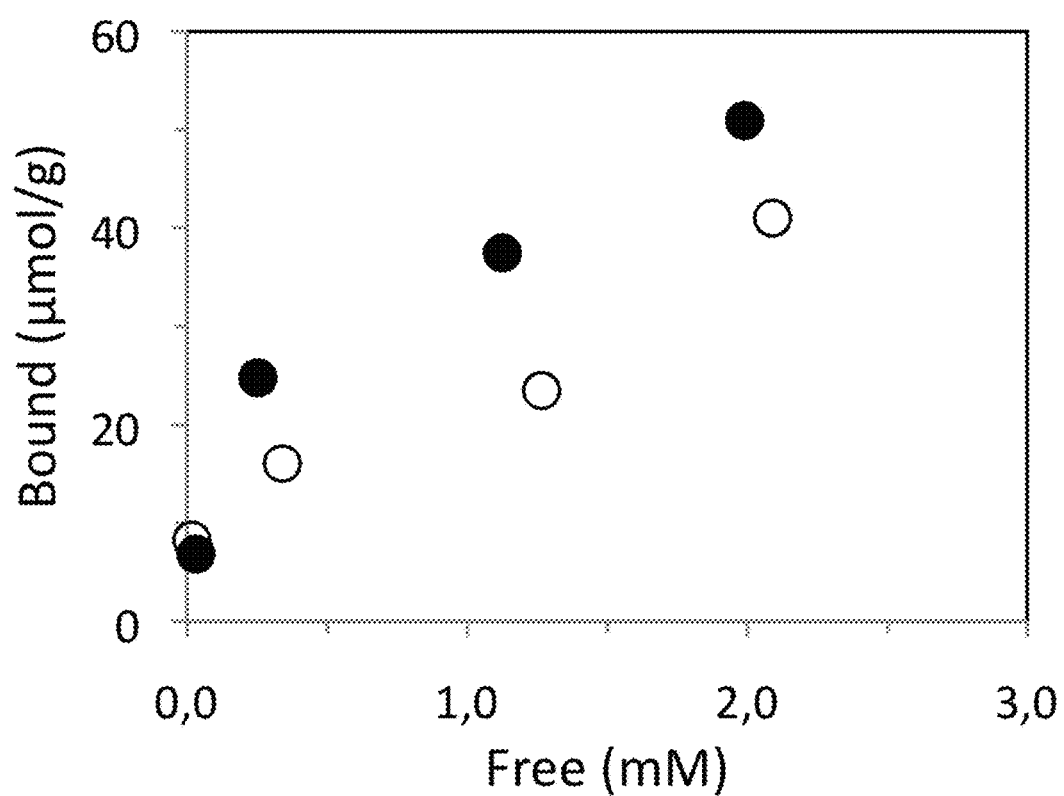
FIG. 12. is a graph of binding curves of L-PA (solid symbols) and D-PA (open symbols) on magNP-LPA imprinted SiNP-MIP2.

10 mg of the imprinted polymer obtained after the washing and removing of template and drying in vacuum oven was weighed into 10 separate HPLC vials. After that, 1 mL of L/D-PA solutions at 1.0 mM in acetonitrile was added to the polymers. The HPLC vials were then sealed and their contents allowed to equilibrate overnight at room temperature with gentle shaking. After 15 h, the polymer particles were separated by centrifugation allowing analysis of the supernatant solutions by HPLC. For the HPLC tests, a commercially available HPLC column, Phenomenex Luna C-18 (250×4.6 mm2) was used. The mobile phase was $H_2O$/MeOH/TFA, 40/60/0.2 v/v pumped at a flow rate of 1 mL/min. The adsorption isotherms were thereafter obtained by plotting the free concentration of L/D-PA over the concentration bound to the polymers using calibration curves for L/D-PA. The isotherms are shown in FIGS. 11 and 12.

Example 9

Figure 9:
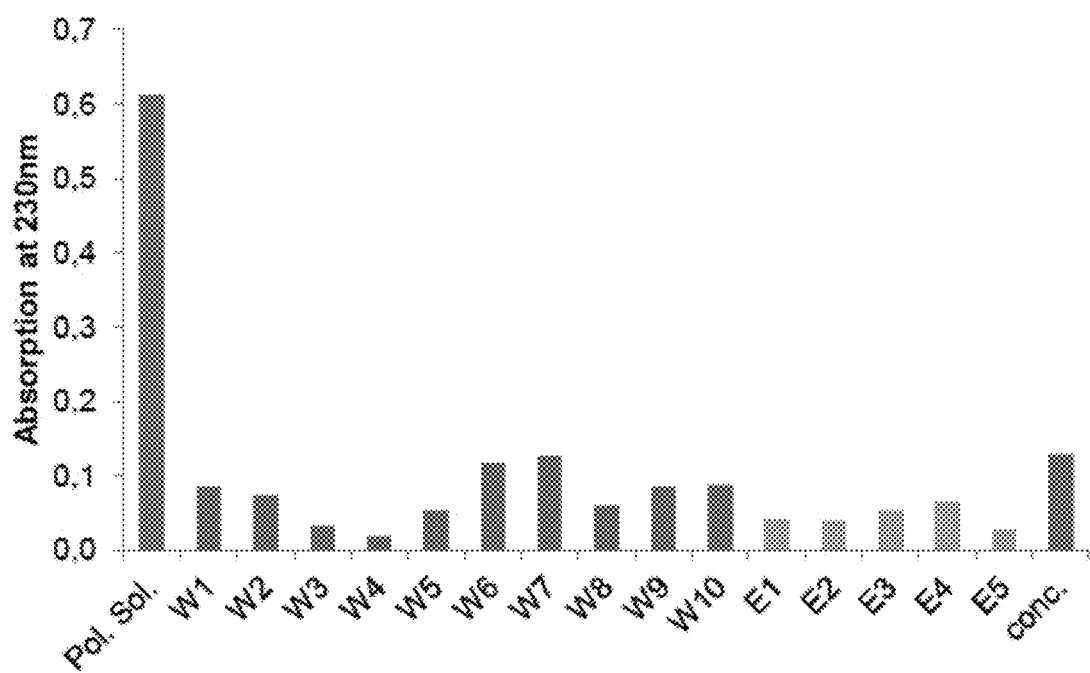
FIG. 9 is a graph of absorption at 230 nm of the polymerization solution (Pol. Sol.), washing fractions using 10 mL water at room temperature (W1-W10), elution fractions using 10 mL water at 60° C. in each step (E1-E5) and concentrated eluates after concentration under vacuum (conc.) as described in Example 9.
Figure 10:
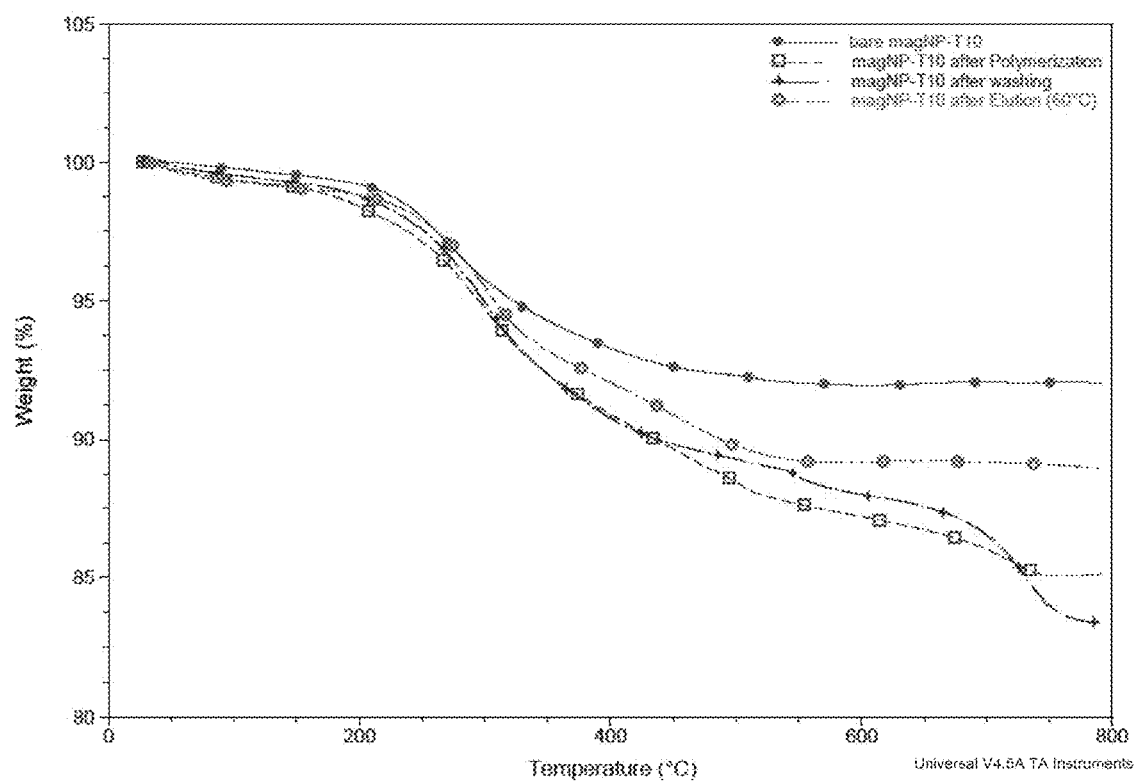
FIG. 10 is a graph of the thermal gravimetric analysis of nanoparticles and nanoparticle aggregates in Example 9, including: magNP-T10 (green trace); crude magNPT10-NP-MIP3 after polymerization (blue trace); magNPT10-NP-MIP3 after washing (brown trace); and magNPT10-NP-MIP3 after elution at 60° C. (purple trace).

Synthesis of Nanoparticles by Precipitation Polymerization Using a Peptide Placeholder Template The monomers for precipitation polymerization, N-isopropylacrylamide (NIPAm) (20 mg; 53%), crosslinker (N,N'-methylenebisacrylamide; BIS) (19 mg; 2%), N-tert-butylacrylamide (TBAm; hydrophobic monomer) (17 mg; 40%), and acrylic acid (AAc) (1.17 mg; 5%) negatively charged monomer were dissolved in 50 mL millipore water with 10 mg SDS. After filtering through membrane filter (pore size: 0.45 μm), 500 mg of magNP-T10 (to give imprinted nanoparticles NP-MIP3), magNP-R10 (to give imprinted nanoparticles NP-MIP4) or ring opened magNP-epoxy (to give nonimprinted nanoparticles NP-N3) was added. The solution was degassed by sonication under vacuum (10 min) followed by nitrogen bubbling for 30 min. Afterwards, the polymerization was initiated by the addition of 30 mg APS in 500 μL water and 15 μL TEMED to the solution. After the polymerization at room temperature overnight, the magnetic particles were collected using a magnet washed with water (room temperature, 10×10 mL). After 10 washing steps, the polymer particles were eluted with water preheated to 60° C. (5×10 mL). After each addition of the eluent, the vial was placed in a water bath at 60° C. for 7 min and the UV absorption at 230 nm in the supernatant measured (FIG. 9). A slight enhancement in the UV absorbtion in the eluted fraction E3-E4 and the results from thermal gravimetric analysis (FIG. 10) proves that strongly adhearing particles had been removed in the elution step.

Example 10

Binding Properties Towards T10, R10 and Immunoglobuline G (IgG)

5 mg of the imprinted polymer obtained after the washing and removing of template and drying in vacuum oven was weighed into 10 separate HPLC vials. After that, 1 mL of T10, R10 (both at 0.1 mg/mL) or the complementary protein IgG (5 mg/mL) solutions in HEPES buffer (0.1M pH 7.5) was added to the polymers. The HPLC vials were then sealed and their contents allowed to equilibrate overnight at room temperature with gentle shaking. After 15 h, the polymer particles were separated by centrifugation allowing analysis of the supernatant solutions using the BCA assay (IgG) or by HPLC (R10 and T10). For the HPLC tests, a commercially available HPLC column, Phenomenex Luna C-18 (250×4.6 mm2) was used and a mobile phase consisting of acetonitrile/water: 20/80 (0.1% TFA). The following uptake was measured for each of the NPs:

| Polymer | Solute | Bound (mg/g) |
|---------|--------|--------------|
| NP-MIP3 | T10 | 10 |
|  | R10 | 6 |
|  | IgG | 93 |
| NP-MIP4 | T10 | 7 |
|  | R10 | 8 |
|  | IgG | 67 |
| NP-N3 | T10 | 6 |
|  | R10 | 5 |
|  | IgG | 44 |

What is claimed is:

1. A process for preparing a surface imprinted polymer, comprising:
   1) providing a multifunctional placeholder template;
   2) polymerizing at least one monomer, optionally dissolved in a solvent, in presence of the multifunctional placeholder template, wherein the multifunctional placeholder template comprises a molecular template connected to a magnetic affinity handle, with a spacer therebetween, forming a crude reaction mixture;
   3) separating the multifunctional placeholder template and polymers adhering to the multifunctional placeholder template from the crude reaction mixture wherein the separation of the multifunctional placeholder template and polymers adhering to the multifunctional placeholder template from the crude reaction mixture is performed by allowing the crude reaction mixture containing the multifunctional placeholder template to be exposed to a magnetic field resulting in magnetic separation of the multifunctional placeholder template and particles adhering to the multifunctional placeholder template from the crude reaction mixture;
   4) gradually releasing the polymer adhering to the multifunctional placeholder template by physical or chemical technique thereby allowing to form molecularly imprinted polymers (MIPs) which bind strongly to the multifunctional template; and
   5) reusing the multifunctional placeholder template and repeating steps 1)-4) for preparing an additional surface imprinted polymer.

2. A process according to claim 1, wherein the molecular template comprises a molecular structure representing a target molecule or a fragment of the target molecule.

3. A process according to claim 1, wherein the molecular template is selected from the group consisting of peptides, glycans, oligonucleotides, and mimics of oligonucleotides.

4. A process according to claim 1, wherein the spacer has a sufficient length to enable the multifunctional placeholder template to bind the adhered polymer and to a stationary phase.

5. A process according to claim 1, wherein the spacer comprises polyethylenglycol, polyglycerol, poly-2-hydroxymethacrylate, or a perfluorinated hydrocarbon chain.

6. A process according to claim 1, wherein the spacer is prepared by controlled radical polymerization allowing the molecular template or the affinity handle to be attached by endgroup functionalization.

7. A process according to claim 1, comprising precipitation polymerization, miniemulsion polymerization, grafting from polymerization, or reversible addition fragmentation chain transfer polymerization (RAFT).

8. A process for preparing a surface imprinted polymer, comprising:
   1) providing a multifunctional placeholder template;
   2) polymerizing at least one monomer, optionally dissolved in a solvent, in presence of the multifunctional placeholder template, forming a crude reaction mixture;
   3) separating the multifunctional placeholder template and polymers adhering to the multifunctional placeholder template from the crude reaction mixture;
   4) gradually releasing the polymer adhering to the multifunctional placeholder template by physical or chemical technique thereby allowing to form molecularly imprinted polymers (MIPs) which bind strongly to the multifunctional template; and 5) reusing the multifunctional placeholder template and repeating steps 1)-4) for preparing an additional surface imprinted polymer, wherein the multifunctional placeholder template comprises a molecular template connected to an affinity handle, with a spacer therebetween, and wherein the separation of the multifunctional placeholder template and polymers adhering to the multifunctional placeholder template from the crude reaction mixture is performed by allowing the crude reaction mixture containing the multifunctional placeholder template to contact a solid stationary phase which is capable of reversibly binding to the affinity handle of the multifunctional placeholder template, thereby leading to separation of the multifunctional placeholder template and particles adhering to the multifunctional placeholder template from the crude reaction mixture.

9. A process according to claim 8, wherein the affinity handle comprises (i) one or several vicinal diol groups or another functional group capable of reversibly forming ester bonds with a boronic acid ligand, or (ii) a thiol or protected thiol group capable of reversibly binding to a disulfide containing stationary phase.

10. A process according to claim 1, wherein gradually releasing the polymer adhering to the multifunctional placeholder template is achieved by increasing or reducing temperature.

11. A process according to claim 1, wherein gradually releasing the polymer adhering to the multifunctional placeholder template is achieved by subjecting the separated placeholder template to (i) solutions of increasing ionic strength, (ii) organic solvents, or (ii) organic solvents with modifiers of increasing concentration.

12. A process according to claim 1, wherein gradually releasing the polymer adhering to the multifunctional placeholder template is achieved by subjecting the separated placeholder template to solutions containing an increasing concentration of a displacer molecule.

13. A process according to claim 1, wherein the surface imprinted polymer contains thiol groups.

* * * * *

UNITED STATES PATENT AND TRADEMARK OFFICE
CERTIFICATE OF CORRECTION

PATENT NO. : 10,435,486 B2
APPLICATION NO. : 15/428091
DATED : October 8, 2019
INVENTOR(S) : Borje Sellergren It is certified that error appears in the above-identified patent and that said Letters Patent is hereby corrected as shown below:

On the Title Page

At Column 1, Lines 10-11, referring to "Swedish Patent Application No. 1430090-9", under the heading "(30) Foreign Application Priority Data", in the following line, should be corrected as follows:
"(SE) .................. 1430090" should be -- (SE) ................ 1430090-9 --.

Signed and Sealed this
Nineteenth Day of November, 2019

Andrei Iancu
*Director of the United States Patent and Trademark Office*